US006639091B2

(12) United States Patent
Drent et al.

(10) Patent No.: US 6,639,091 B2
(45) Date of Patent: Oct. 28, 2003

(54) BIDENTATE LIGAND, CATALYST SYSTEM CONTAINING SUCH LIGAND AND A PROCESS FOR THE CARBONYLATION OF ETHYLENICALLY OR ACETYLENICALLY UNSATURATED COMPOUNDS USING SUCH A CATALYST SYSTEM

(75) Inventors: Eit Drent, Amsterdam (NL); Michael Rolf Eberhard, Bristol (GB); Paul Gerard Pringle, Bristol (GB)

(73) Assignee: Shell Oil Company, Houston, TX (US)

( * ) Notice: Subject to any disclaimer, the term of this patent is extended or adjusted under 35 U.S.C. 154(b) by 2 days.

(21) Appl. No.: 09/860,015

(22) Filed: May 17, 2001

(65) Prior Publication Data

US 2002/0016484 A1 Feb. 7, 2002

(30) Foreign Application Priority Data

May 17, 2000 (EP) .......................................... 00304171

(51) Int. Cl.[7] .......................... C07F 9/02; B01J 31/00; C07C 67/00; C07C 45/00

(52) U.S. Cl. .......................... 556/21; 556/18; 502/162; 502/167; 560/204; 560/233; 560/239; 562/519; 568/8; 568/12; 568/451

(58) Field of Search ........................ 556/18, 21; 568/8, 568/12, 451; 560/204, 233, 239; 562/519; 502/162, 167

(56) References Cited

U.S. PATENT DOCUMENTS 3,527,818 A 9/1970 Mason et al. ............... 260/632
5,495,041 A 2/1996 Sielcken et al. ............ 560/207

FOREIGN PATENT DOCUMENTS

| | | | |
|---|---|---|---|
| CA | 2086285 | 6/1994 | ............ C07F/9/50 |
| EP | 0495547 A2 | 7/1992 | ........... C07C/51/14 |
| EP | 0 495 548 A2 * | 10/1992 | |
| WO | WO 95/05354 | 2/1995 | ........... C07C/29/16 |
| WO | WO 98/42717 | 10/1998 | ......... C07F/9/6568 |
| WO | WO 00/14055 | 3/2000 | ......... C07C/253/00 |

OTHER PUBLICATIONS

U.S. patent application Ser. No. 09/804,891, Drent et al., filed Mar. 13, 2001.

* cited by examiner

*Primary Examiner*—Porfirio Nazario-Gonzalez

(57) ABSTRACT

Bidentate ligand of formula II, $$R^1R^2M^1—R—M^2R^3R^4 \quad (II)$$

wherein $M^1$ and $M^2$ are independently P, As or Sb; $R^1$, $R^2$, $R^3$ and $R^4$ independently represent tertiary alkyl groups, or $R^1$ and $R^2$ together and/or $R^3$ and $R^4$ together represent an optionally substituted bivalent cycloaliphatic group whereby the two free valencies are linked to $M^1$ or $M^2$, and R represents a bivalent aliphatic bridging group containing from 2 to 6 atoms in the bridge, which is substituted with two or more substituents. A catalyst system comprising:

a) a source of group VIII metal cations;

b) a source of such a bidentate ligand; and c) a source of anions, and use of such a catalyst system in a process for the carbonylation of optionally substituted ethylenically or acetylenically unsaturated compounds by reaction with carbon monoxide and a coreactant is provided.

32 Claims, No Drawings

BIDENTATE LIGAND, CATALYST SYSTEM CONTAINING SUCH LIGAND AND A PROCESS FOR THE CARBONYLATION OF ETHYLENICALLY OR ACETYLENICALLY UNSATURATED COMPOUNDS USING SUCH A CATALYST SYSTEM

This invention relates to a bidentate ligand of formula I, $$Q^1Q^2V^1—Q—V^2Q^3Q^4 \quad (I)$$

wherein $V^1$ and $V^2$ are independently P, As or Sb; $Q^1$, $Q^2$, $Q^3$ and $Q^4$ represent hydrocarbyl groups and R represents a bivalent bridging group. The invention further relates to a catalyst system containing such a bidentate ligand, a source of group VIII metal cations and a source of anions. Moreover, the invention relates to a process for the carbonylation of optionally substituted ethylenically or acetylenically unsaturated compounds by reaction with carbon monoxide and a coreactant in the presence of such a catalyst system.

BACKGROUND OF THE INVENTION

One commercially important carbonylation reaction using hydrogen as coreactant, is the hydroformylation of alkenes or alkynes, which are reacted with carbon monoxide and hydrogen in the presence of transition metal catalysts to form aldehydes and/or alcohols having one carbon atom more than the precursor alkene or alkyne.

Depending on catalyst, reaction conditions and substrates, the hydroformylation may proceed with varying selectivities to the several possible isomeric aldehydes or alcohols in varying yields, as side reactions occur to a smaller or larger extent. Generally only one isomeric product is preferred. For many applications the presence of branched aldehydes or alcohols is undesirable. Moreover, in view of biological degradability, it is considered advantageous to obtain products having a high content of the linear isomer. The selectivity towards one of several possible isomeric products is called regioselectivity. For hydroformylation a regioselectivity towards reaction at the primary carbon atom, resulting in a linear product, is desirable.

Another commercially important carbonylation reaction using an alkanol or water as coreactant, is the carbonylation of alkenes or alkynes, which are reacted with carbon monoxide and alkanol in the presence of Group VIII metal catalysts to form esters, diesters or carboxylic acids. An example of such a carbonylation is the reaction of ethene with carbon monoxide and butanol to prepare butylpropionates.

CA-A-2086285 relates to the preparation of diphosphines, wherein an alkane, alkene or arene is vicinally disubstituted with two organophosphino groups. The bidentate diphosphines are said to be useful in the preparation of catalysts for the preparation of polyketones. In example 13 the preparation of 2,3 bis(di-isobutylphosphino)pentane) is described.

WO 9505354 describes the hydroformylation of ethylenically unsaturated compounds by reaction with carbon monoxide and hydrogen in the presence of a catalyst system comprising a Group VIII metal cation, viz. cationic palladium, and a bidentate ligand, viz. a diphosphine. In the examples several bidentate diphosphines are used. As is illustrated by examples 46 and 47 the hydroformylation of 1-octene with a catalyst system containing a bidentate diphosphine results in acceptable selectivities towards the linear product. The results show that the use of a bidentate diphosphine having an unsubstituted bivalent organic bridging group, connecting both phosphorus atoms, i.e. 1,2-bis-(1,4-cyclooctylenephosphino)ethane, results in higher selectivities towards the linear product than the use of a bidentate diphosphine having a monosubstituted bivalent organic bridging group, connecting both phosphorus atoms, i.e. 1,2-bis(1,4-cyclooctylenephosphino)propane. Hence, this patent document suggests that non-substituted bridging groups are advantageous compared to substituted bridging groups.

Although good results with regard to this regioselectivity towards the linear product are obtained in WO 9505354, there is still room for improvement. This need especially exists with regard to smaller ethylenically unsaturated compounds, where side-reactions more readily occur.

Examples 28 to 36 of EP-A-0495547 describe a carbonylation of ethene with carbon monoxide and n-butanol in the presence of bidentate diphosphines having an unsubstituted bivalent organic bridging group, connecting both phosphorus atoms, i.e. 1,3-bis(di-isopropylphosphino)propane; 1,3-bis(di-ethylphosphino)propane; 1,3-bis(di-s-butylphosphino)propane, 1,3-bis-(di-phenylphosphino) propane. Selectivities of 98% and rates of conversion in the range from 100 to 1000 mol butylpropionate/mol Pd/hr are obtained.

Although good results with regard to selectivity and activity are obtained in EP-A-0495547, there is still room for improvement.

SUMMARY OF THE INVENTION

Accordingly this invention provides a bidentate ligand of formula II, $$R^1R^2M^1—R—M^2R^3R^4 \quad (II)$$

wherein $M^1$ and $M^2$ are independently P, As or Sb; $R^1$, $R^2$, $R^3$ and $R^4$ independently represent tertiary alkyl groups, or $R^1$ and $R^2$ together and/or $R^3$ and $R^4$ together represent an optionally substituted bivalent cycloaliphatic group whereby the two free valencies are linked to $M^1$ or $M^2$, and R represents a bivalent aliphatic bridging group containing from 2 to 6 atoms in the bridge, which is substituted with two or more substituents.

Further, a catalyst system comprising a) a source of group VIII metal cations, b) a source of such a bidentate ligand, and c) a source of anions is provided. A process for the carbonylation of optionally substituted ethylenically or acetylenically unsaturated compounds comprising reacting the unsaturated compounds with carbon monoxide and a coreactant in the presence of such a catalyst system is also provided.

DETAILED DESCRIPTION OF THE INVENTION

It has now surprisingly been found that when carbonylation is carried out in the presence of a catalyst system that is characterized by a specific choice of bidentate ligand containing a polysubstituted bridging group, unexpected advantages with regard to the regioselectivity and/or activity are obtained. It was found that a catalyst system comprising such a bidentate ligand having a polysubstituted bivalent aliphatic bridging group results in a high regioselectivity towards the linear product and/or a higher activity.

In the bidentate ligand of formula II, $M^1$ and $M^2$ are preferably the same and more preferably they both represent phosphorus atoms.

By "a bridge" is understood the shortest connection between the atoms $M^1$ and $M^2$. This bridge can be saturated or non-saturated or can form part of an optionally substituted saturated or non-saturated aliphatic ring structure, comprising one or more rings. The bridge can further contain heteroatoms such as nitrogen, sulphur, silicon or oxygen atoms. Preferably at least the atoms in the bridge connected to $M^1$ and $M^2$ are carbon atoms, more preferably all atoms in the bridge are carbon atoms.

The bridge connecting $M^1$ and $M^2$ forms part of a bridging group R, which can be saturated or unsaturated and which can be an optionally substituted saturated or non-saturated aliphatic ring structure, such as for example cyclohexane, cyclohexene, cyclopentane or cyclopentene. The bridging group can further contain heteroatoms such as nitrogen, sulphur, silicon or oxygen atoms. Unsaturated bonds and/or heteroatoms can be present in each part of the bridging group R, both within and outside the bridge. If the bridging group R is a cycloaliphatic ring structure, the ring may be interrupted by one or more heteroatoms such as nitrogen, sulphur, silicon or oxygen atoms. The aliphatic ring structure can further be substituted with any kind of substituent, including heteroatoms, alkylgroups, cycloalkyl groups and aryl groups, both within as well as outside the bridge.

The bivalent aliphatic bridging group R, connecting the atoms $M^1$ and $M^2$ contains from 2 to 6 atoms in the bridge, more preferably 2 to 4 atoms, and most preferably 2 to 3 atoms. Preferably the atoms in the bridge are carbon atoms. Bivalent aliphatic bridging groups R, containing 2 carbon atoms in the bridge are especially preferred.

The bridge is substituted with at least two substituents. Preferably the bridge is substituted with two to four substituents and more preferably with two to three substituents. Most preferably the bridge is substituted with two substituents. The substituents can be substituted to any part of the bridge, but are preferably substituted on carbon atoms of the bridging group connected to $M^1$ and $M^2$. A preferred bridging group is thus a bridging group R having from 2 to 6 carbon atoms in the bridge, wherein the carbon atoms of the bridging group connected to $M^1$ and $M^2$ are both substituted with at least one substituent. The carbon atoms of the bridging group connected to $M^1$ and $M^2$ are preferably substituted with only one substitutent, but they can be substituted with two substituents.

In addition to the carbon atoms connected to $M^1$ and $M^2$, the bridging group can be substituted at other parts, with any kind of substituent, including heteroatoms, alkylgroups, cycloalkyl groups and aryl groups.

In case the substituents are substituted at carbon atoms of the bridge connected to the atoms $M^1$ and $M^2$, the bidentate ligand has chiral C-atoms and can have a R,R, S,S or R,S meso form or mixtures thereof. Both the meso form as well as racemic mixtures can be used.

The substituents on the bridge can be independent or connected. If the substituents are connected, the whole of the substituents and the bridge together can form a bridging group that is an aliphatic ring structure as described herein before. The substituents can further contain carbon atoms and/or hetero atoms.

Suitable substituents include groups containing heteroatoms such as halides, sulphur, phosphorus, oxygen and nitrogen. Examples of such groups include chloride, bromide, iodide, thiol, and groups of the general formula H—O—, $X^1$—O—, —S—$X^1$, —CO—$X^1$, —$NH_2$, —$NHX^1$, —$NX^1X^2$, —CO—$NX^1X^2$, —OH, —$PO_4$, —$NO_2$, —NOH, —CO, —$SO_2$, —SOH, in which $X^1$ and $X^2$, independently, represent aliphatic groups, preferably having from 1 to 10 carbon atoms, more preferably having from 1 to 4 carbon atoms, like methyl, ethyl, propyl and isopropyl.

Preferably the substituents are hydrocarbyl groups. The hydrocarbyl groups itself can be aromatic, aliphatic or cycloaliphatic. The hydrocarbyl groups can contain carbon atoms and hetero atoms. Suitable hydrocarbyl groups can further include groups containing hetero-atoms such as the ones mentioned hereinabove. The hydrocarbyl groups include straight-chain or branched saturated or non-saturated carbon containing groups.

Suitable aromatic hydrocarbyl groups include aryl groups such as phenyl groups or naphtyl groups, and alkyl phenyl groups such as tolyl groups. Of these, substitution with phenyl groups is preferred.

Preferably the hydrocarbyl groups are alkyl groups, preferably having from 1 to 10 carbon atoms, more preferably from 1 to 4 carbon atoms. Linear, branched or cyclic alkyl groups can be used. Suitable alkyl groups include, methyl, ethyl, propyl, iso-propyl, butyl and iso-butyl. More suitably methyl groups are used.

Most preferably the bridge is di-substituted, preferably with two alkyl groups, most preferably with two methyl groups. In an advantageous embodiment the substitution is vicinal.

Examples of bivalent aliphatic bridging groups that can be used include cyclopentane, cyclopentene, cyclohexane, cyclohexene, butane, 1-butene, 2-butene, pentane, 2-pentene, diphenylethane, diethylether, 1,2-diphenylpropane, 2,3-diphenylbutane.

$R^1$, $R^2$, $R^3$ and $R^4$ can independently represent a tertiary alkyl group. By a tertiary alkyl group is understood an alkyl group which is connected to the phosphorus atom by a tertiary carbon atom. The tertiary alkyl group preferably has from 4 to 20 carbon atoms, more preferably from 4 to 8 carbon atoms. Examples of suitable non-cyclic tertiary alkyl groups are tertiary butyl, 2-(2-methyl)butyl, 2-(2-ethyl)butyl, 2-(2-methyl)pentyl and 2-(2-ethyl)pentyl groups. Preferably the groups $R^1$ to $R^4$ represent the same tertiary alkyl groups, most preferably $R^1$ to $R^4$ are tert-butyl groups.

Example of ligands include 2,3-bis(di-tertiary-butylphosphino)butane, 2,3-bis(di-tertiary-butylphosphino)butene, 2,4-bis(di-tertiarybutylphosphino)pentane, 2,4-bis(di-tertiarybutylphosphino)pentene, 1,2-bis(di-tertiarybutylphosphino)cyclopentane, 1,2-bis(di-tertiarybutylphosphino)pent-1-ene, 2,3-bis(di-tertiary-butylphosphino)pentane, 2,4-bis(di-tertiary-butylphosphino)hexane, 3,4-bis(di-tertiary-butylphosphino)hexane, 2,3-bis[di-2-(2-methyl)butylphosphino]butane, 2,3-bis[di-2-(2-ethyl)butylphosphino]butane. A very suitable bidentate diphosphine is 2,4-bis(di-tertiarybutylphosphino)pentane.

$R^1$ and $R^2$ together and/or $R^3$ and $R^4$ together can also represent an optionally substituted bivalent cycloaliphatic group.

A special class of bivalent cycloaliphatic groups include tertiary cyclic structures. For example $R^1$ and $R^2$ and/or $R^3$ and $R^4$ can represent a bivalent radical that together with the phosphorus atom to which it is attached is an alkyl substituted 2-phosphatricyclo[3.3.1.1{3,7}]-decyl group or a derivative thereof in which one or more of the carbon atoms are replaced by heteroatoms. Preferably the ligand comprising the alkyl substituted 2-phospha-tricyclo[3.3.1.1{3,7}] decyl group is a compound according to Formula III, wherein $R^5$ are alkyl groups of 1–6 carbon atoms, preferably methyl.

(III)

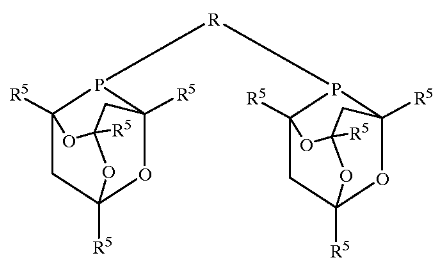

Example of ligands include 2,3-P,P'-di(2-phospha-1,3,5,7-tetramethyl-6,9,10-trioxatricyclo-[3.3.1.1{3.7}]decyl) butane and 2,4-P,P'-di(2-phospha-1,3,5,7-tetramethyl-6,9,10-trioxatricyclo[3.3.1.1{3.7}]-decyl)pentane. Such ligands can be prepared as described in more detail in WO-A-9842717.

In an especially preferred embodiment $R^1$ and $R^2$ together and/or $R^3$ and $R^4$ together represent an optionally substituted bivalent cycloaliphatic group. More preferably both $R^1$ and $R^2$ together and $R^3$ and $R^4$ together represent such an optionally substituted bivalent cycloaliphatic group. This optionally substituted bivalent cycloaliphatic group preferably comprises at least 5 ring atoms and more preferably contains from 6 to 10 ring atoms. It is advantageous that the cycloaliphatic group is a cycloalkylene group, i.e. forming with the atom $M^1$ or $M^2$ a bicyclic group. Preferably $M^1$ and $M^2$ are both phosphorus and $R^1$, $R^2$ and $M^1$ together and $R^3$, $R^4$ and $M^2$ together both represent a phosphabicylocalkyl group. In a highly preferred embodiment the cyclic group contains 8 ring atoms and forms a 9-phosphabicyclononyl group together with a phosphorus atom. The 9-phosphabicyclononyl group can have several isomeric structures. For the purpose of the invention the [3,3,1] and [4,2,1] isomers are preferred. $R^1$ and $R^2$ together and $R^3$ and $R^4$ together can have both the same or each a different isomeric structure. Preferably both $R^1$ and $R^2$ together and $R^3$ and $R^4$ together have the [3,3,1] structure. Compositions of bidentate diphosphines having a high amount of bidentate diphosphine ligand having the [3,3,1] structure for both phosphabicyclononyl groups can be prepared as described in non-pre-published European patent application No. 01300866.9.

Substituents of the bivalent cycloaliphatic group formed by $R^1$ together with $R^2$ or $R^3$ together with $R^4$, if any, can be alkyl groups having from 1 to 4 carbon atoms. As a rule, all ring atoms are carbon atoms, but bivalent cyclic groups containing one or more heteroatoms in the ring, such as for example oxygen or nitrogen, atoms are not precluded. Examples of suitable bivalent cyclic groups are 1,4-cyclohexylene, 1,4-cycloheptylene, 1,3-cycloheptylene, 1,2-cyclooctylene, 1,3-cyclooctylene, 1,4-cyclooctylene, 1,5-cyclooctylene, 2-methyl-1,5-cyclo-octylene, 2,6-dimethyl-1,4-cyclooctylene and 2,6-dimethyl-1,5-cyclooctylene groups. Preferred bivalent cyclic groups are selected from 1,4-cyclo-octylene, 1,5-cyclo-octylene, and methyl (di) substituted derivatives thereof.

Examples of preferred bidentate ligands include 2,3-PP'bis(9-phosphabicyclo[3,3,1]nonyl)-butane, 2,3-PP'bis(9-phosphabicyclo[4,2,1]nonyl)-butane, 2,3-PP'bis(9-phosphabicyclo[3,3,1]nonyl)-but-2-ene, 2,3-PP'bis(9-phosphabicyclo[4,2,1]nonyl)-but-2-ene, 2,3-PP'bis(9-phosphabicyclo[3,3,1]nonyl)-pentane, 2,4-PP'bis(9-phosphabicyclo[3,3,1]nonyl)-pentane, 2,3-PP'bis(9-phosphabicyclo[4,2,1]nonyl)-pentane, 2,4-PP'bis(9-phosphabicyclo[4,2,1]nonyl)-pentane, 2,3-PP'bis(9-phosphabicyclo[3,3,1]nonyl)-pent-2-ene, 2,3-PP'bis(9-phosphabicyclo[4,2,1]nonyl)-pent-2-ene, 1,2-PP'bis(9-phosphabicyclo[3,3,1]nonyl)-cyclopentane, 1,2-PP'bis(9-phosphabicyclo[4,2,1]nonyl)-cyclopentane, 1,2-PP'bis(9-phosphabicyclo[3,3,1]nonyl)-cyclohexane, 1,2-PP'bis(9-phosphabicyclo[4,2,1]nonyl)-cyclohexane and mixtures thereof.

These ligands can be prepared by reacting P-cyclo-octylene hydride (phosphabicyclononane hydride) and butyllithium to generate a lithium cyclo-octylene phosphide (lithiated phosphabicyclononane). The later phosphide is reacted with an aliphatic group substituted with suitable leaving groups, preferably tosylates or cyclic sulfates, in an appropriate manner. Preferred aliphatic groups are those having a cyclic sulfate structure as a leaving group, such as cyclic substituted or non-substituted alkane diol sulfate esters, also called cyclic alkyl sulfates. For example 2,4-PP'bis(9-phosphabicyclo[3,3,1]nonyl)-pentane can be prepared by reacting phosphabicyclononane hydride and butyllithium to generate the corresponding lithium phosphide and subsequently reacting this lithium phosphide, at for example 0° C. or ambient temperature (25° C.) in tetrahydrofuran, with 2,4 pentanediol di-p-tosylate ester. 2,3-PP'bis(9-phosphabicyclo[3,3,1]nonyl)-butane can for example be prepared by reacting phosphabicyclononane hydride and butyllithium to generate the corresponding lithium phosphide and subsequently reacting this lithium phosphide with 2,3-butanediol cyclic sulfate ester (IUPAC name cyclic 2,3-butyl sulfate), in for example tetrahydrofuran at a temperature varying in the range from 0° C. to reflux temperature.

The P-cyclo-octylene hydride (phoshabicyclononane hydride) may conveniently be prepared as described by Elsner et al. (Chem. Abstr. 1978, vol. 89, 180154x).

The invention further provides a catalyst system including:

(a) a source of group VIII metal cations;

(b) a bidentate ligand as described above; and (c) a source of anions.

In the present specification the group VIII metals are defined as the metals rhodium, nickel, palladium, platinum, and mixtures thereof. Of these, palladium and platinum are preferred.

Examples of suitable metal sources are platinum and/or palladium compounds such as salts of palladium and/or platinum and nitric acid, sulphuric acid or sulphonic acids, salts of platinum or palladium and carboxylic acids with up to 12 carbon atoms, palladium- or platinum complexes, e.g. with carbon monoxide or acetylacetonate, or palladium or platinum combined with a solid material such as an ion exchanger. Palladium(II) acetate and platinum(II) acetylacetonate are examples of preferred metal sources.

As anion source, any compound generating these anions may be used. Suitably, acids, or salts thereof, are used as source of anions, for example any of the acids mentioned above, which may also participate in the salts of the metals of the platinum group.

In the catalyst systems of the invention, preferably acids are used as anion source having a pKa value of less than 6, more preferably less than 5, measured in aqueous solution at 18° C.

Typical examples of suitable anions are anions of carboxylic acids, phosphoric acid, sulphuric acid, sulphonic acids and halogenated carboxylic acids such as trifluoroacetic acid.

Carboxylic acids that can be used include carboxylic acids with up to 12 carbon atoms, such as for example, pentanoic acid, pivalic acid, propionic acid and propenoic acid.

Sulphonic acids are in particular preferred, for example methanesulphonic acid, trifluoromethanesulphonic acid, tert-butane-sulphonic acid, p-toluenesulphonic acid and 2,4,6-trimethylbenzene-sulphonic acid.

Also, complex anions are suitable, such as the anions generated by a combination of a Lewis acid such as $BF_3$, $AlCl_3$, $SnF_2$, $Sn(CF_3SO_3)_2$, $SnCl_2$ or $GeCl_2$, with a protic acid, such as a sulphonic acid, e.g. $CF_3SO_3H$ or $CH_3SO_3H$ or a hydrohalogenic acid such as HF of HCl, or a combination of a Lewis acid with an alcohol. Examples of such complex anions are $BF_4$—, $SnCl_3$—, $[SnCl_2.CF_3SO_3]$— and $PF_6$—.

The invention further provides a process for the carbonylation of optionally substituted ethylenically or acetylenically unsaturated compounds by reaction with carbon monoxide and a coreactant in the presence of a catalyst system as described above.

The ethylenically or acetylenically unsaturated compound, used as starting material, is preferably an ethylenically or acetylenically unsaturated compound having from 2 to 20 carbon atoms per molecule, or a mixture thereof. They may comprise one or more unsaturated bonds per molecule. Preferred are compounds having from 2 to 6 carbon atoms, or mixtures thereof. The ethylenically or acetylenically unsaturated compound can further comprise functional groups or heteroatoms, such as nitrogen, sulphur or oxide. Examples include unsaturated carboxylic acids, esters of such acids or alkene nitriles.

In a preferred embodiment the ethylenically or acetylenically unsaturated compound is an olefin or mixture of olefins. In a preferred process of the invention, such olefins can be converted by reaction with carbon monoxide and a coreactant with a high regioselectivity towards the linear product. Suitable ethylenically or acetylenically unsaturated compounds include for example acetylene, ethene, propene, butene, isobutene, pentene, pentene nitrites and methyl 3-pentenoates.

In the process of the invention, the unsaturated starting material and the formed product may act as reaction diluent. Hence, the use of a separate solvent is not necessary. Conveniently, however, the carbonylation reaction may be carried out in the additional presence of a solvent. As such, saturated hydrocarbons, e.g. paraffins and isoalkanes are recommended and furthermore alcohols, the saturated hydrocarbons and alcohols preferably having from 4 to 10 carbon atoms per molecule, such as butanol, ethylhexanol-1, nonanol-1, or in general terms the alcohols formed as carbonylation product; ethers such as 2,5,8-trioxanonane (diglyme), diethylether and anisole, and ketones, such as methylbutylketone. Solvents, comprising or substantially consisting of sulphones are also preferred. Sulphones are in particular preferred, for example dialkylsulphones such as dimethylsulphone and diethylsulphone and cyclic sulphones, such as sulfolane (tetrahydrothiophene-2,2-dioxide), sulfolane, 2-methylsulfolane and 2-methyl-4-ethyl-sulfolane.

The quantity in which the catalyst system is used, is not critical and may vary within wide limits. Usually amounts in the range of $10^{-8}$ to $10^{-1}$, preferably in the range of $10^{-7}$ to $10^{-2}$ mole atom of Group VIII metal per mole of ethylenically unsaturated compound are used. The amounts of the participants in the catalyst system are conveniently selected such that per mole atom of platinum group metal from 0.5 to 10, preferably from 1 to 6 moles of bidentate ligand are used, from 0.5 to 15, preferably from 1 to 8 moles of anion source or a complex anion source.

Furthermore the presence of a small amount of catalyst promoter comprising a source of halide anions, such as for example HI or HCl, can have a significant favourable effect in that the conversion reaction proceeds at high rate, even at moderate temperatures.

For hydroformylation the coreactant can be molecular hydrogen, or more generally a hydride source The carbon monoxide and hydrogen may be supplied in equimolar or non-equimolar ratios, e.g. in a ratio within the range of 5:1 to 1:5, preferably 3:1 to 1:3. Preferably they are supplied in a ratio within the range of 2:1 to 1:2.

The ethylenically or acetylenically unsaturated compound is reacted with carbon monoxide and a coreactant under conditions effective to carbonylate the unsaturated bond of the unsaturated compound. The carbonylation can be suitably carried out at moderate reaction conditions. Hence temperatures in the range of about 50 to about 200° C. are recommended, preferred temperatures being in the range of about 70 to about 160° C. Reaction pressures in the range of about 5 to about 100 bar are preferred, lower or higher pressures may be selected, but are not considered particularly advantageous. Moreover, higher pressures require special equipment provisions.

The claimed catalyst system can also be useful in conversion reactions other than hydroformylation. In general the coreactant can be represented by NuH, wherein Nu represents the remnant nucleophilic moiety of the coreactant after removal of a hydrogen atom. The nature of the coreactant largely determines the type of product formed. Preferably the coreactant is a nucleophilic compound having a mobile hydrogen atom, such as an alcohol, an acid, an amine or water. For an alcohol XOH (X being the carbon containing part), the XO moiety is represented by Nu and accordingly the product is an ester.

Similarly, the use of an acid XCOOH (Nu=XCOO) will introduce an anhydride group in the product of the monocarbonylation reaction; the use of ammonia ($Nu{=}NH_2$) or an amine $XNH_2$ (Nu=XNH) or $X_2NH$ ($Nu{=}X_2N$) will introduce an amide group; the use of a thiol XSH (Nu=XS) will introduce a thioester group; and the use of water (Nu=OH) will introduce a carboxy group.

Preferred coreactants are water, alkanol and hydrogen.

Preferred alkanols are alkanols with 1 to 20, more preferably with 1 to 6 carbon atoms per molecule and alkanediols with 2–20, more preferably 2 to 6 carbon atoms per molecule. The alkanols can be aliphatic, cycloaliphatic or aromatic. Suitable alkanols in the process of the invention include methanol, ethanol, ethanediol, n-propanol, 1,3-propanediol, iso-propanol, butanol, iso-butanol, tert.butanol, pentanol, hexanol, cyclohexanol and phenol.

The invention will be illustrated by the following non-limiting examples.

EXAMPLE 1

Example 1 was carried out in a 250 ml magnetically stirred autoclave. The autoclave was charged with 10 ml of propene, 40 ml anisole and 10 ml sulfolane, 0.25 mmol of platinum(II) acetylacetonate, 0.3 mmol of meso (R,S) 2,3-bis[cyclo-octylene)phosphino]butane, 0.3 mmol $SnCl_2$ and 0.3 mmol HCl. After being flushed, the autoclave was pressurized with carbon monoxide and hydrogen to a partial pressure of 30 bar of each. Subsequently, the reactor was sealed and the contents were heated to 100° C. and maintained at that temperature until the reaction was substantially complete. Complete propene conversion occurred in 0.5 hr, the initial rate of carbonylation was 1000 mol CO/grams atom platinum/hour. The initial rate of carbonylation was defined as the mean rate of carbon monoxide consumption over the first 30% propene conversion. After cooling, a sample was taken from the contents of the reactor and analysed by Gas Liquid Chromatography. The selectivity towards the linear product n-butyraldehyde was 99.0%.

Comparative Example A

Example 1 was repeated, except that instead of 0.3 mmol meso 2,3 bis[(cyclo-octylene)phosphino]butane, 0.3 mmol ligand 1,2 bis[(cyclo-octylene)phosphino]ethane was used as ligand. A similar rate of reaction was observed. After analysis by Gas Liquid Chromatography it was found that the selectivity towards the linear product n-butyraldehyde was 95.5%.

EXAMPLE 2

Example 2 was carried out in a 250 ml magnetically stirred autoclave. The autoclave was charged with 50 ml of butanol, 0.25 mmol of palladium(II) acetate, 0.33 mmol of meso (R,S) 2,3-PP'bis(phosphabicyclo[3.3.1]nonyl)butane, 0.75 ml priopionic acid, and 0.025 mmol HI. After being flushed, the autoclave was pressurized with carbon monoxide to a partial pressure of 15 bar and ethene to a partial pressure of 10 bar. Subsequently, the reactor was sealed and the contents were heated to 115° C. and maintained at that temperature during 1 hour. The initial rate of carbonylation was 1490 mol CO/grams atom palladium/hour. The initial rate of carbonylation was defined as the mean rate of carbon monoxide consumption over the first 30% ethene conversion. After cooling, a sample was taken from the contents of the reactor and analysed by Gas Liquid Chromatography. Conversion was essentially 100%. The selectivity towards butylpropionate was 99%.

Comparative Example B

Example 2 was repeated, except that instead of 0.33 mmol of meso (R,S) 2,3-PP'bis(phosphabicyclo[3.3.1]-nonyl) butane, 0.4 mmol 1,2-PP'bis(9-phosphabicyclononyl)-ethane) was used as ligand. The initial rate of carbonylation was 840 mol CO/grams atom palladium/hour. Conversion was essentially 100%. A similar selectivity towards butylpropionate was observed.

EXAMPLE 3

Example 3 was carried out in a 250 ml magnetically stirred autoclave. The autoclave was charged with 30 ml of butanol-1, 0.25 mmol of platinum(II) acetylacetonate, 0.3 mmol of meso (R,S) 2,3-PP'bis(phosphabicyclo[3.3.1] nonyl)butane, 30 ml diglyme, 0.3 mmol phosphoric acid. After being flushed, the autoclave was pressurized with carbon monoxide to a partial pressure of 30 bar and acetylene to a partial pressure of 1.5 bar. Subsequently, the reactor was sealed and the contents were heated to 125° C. and maintained at that temperature during 5 hour. The initial rate of carbonylation was 2500 mol CO/grams atom platinum/hour. Conversion was essentially 100%. The selectivity towards butylacrylate was 98%.

Comparative Example C

Example 2 was repeated, except that instead of 0.33 mmol of meso (R,S) 2,3-PP'bis(phosphabicyclo[3.3.1]-nonyl) butane, 0.4 mmol 1,2-PP'bis(9-phosphabicyclononyl)-ethane) was used as ligand. The initial rate of carbonylation was 1270 mol CO/grams atom platinum/hour. Conversion was 80%. The selectivity towards butylacrylate was 98%.

We claim:

1. A bidentate ligand of formula II, $$R^1R^2M^1—R—M^2R^3R^4 \quad (II)$$

wherein $M^1$ and $M^2$ are independently P, As or Sb; $R^1$ and $R^2$ together and/or $R^3$ and $R^4$ together represent an optionally substituted bivalent cycloaliphatic group whereby the two free valencies are linked to $M^1$ or $M^2$, and R represents a bivalent aliphatic bridging group containing from 2 to 6 atoms in the bridge, which is substituted with at least two substituents.

2. The bidentate ligand of claim 1 wherein both $M^1$ and $M^2$ are phosphorus atoms.

3. The bidentate ligand of claim 1 wherein the bridging group contains from 2 to 4 carbon atoms in the bridge.

4. The bidentate ligand of claim 1 wherein substituents are substituted at carbon atoms of the bridging group connected with the atoms $M^1$ and $M^2$.

5. The bidentate ligand of claim 4 wherein the bridging group contains from 2 to 4 carbon atoms in the bridge.

6. The bidentate ligand of claim 5 wherein both $M^1$ and $M^2$ are phosphorus atoms.

7. The bidentate ligand of claim 4 wherein the substituents are alkyl groups.

8. The bidentate ligand of claim 1 wherein the substituents are alkyl groups.

9. The bidentate ligand of claim 1 wherein $R^1$ and $R^2$ and/or $R^3$ and $R^4$ together represent a bivalent substituted or non-substituted cycloalkylene group having from 6 to and including 9 ring atoms, whereby the two free valencies are linked to $M^1$ or $M^2$.

10. The bidentate ligand of claim 9 wherein both $M^1$ and $M^2$ are phosphorus atoms.

11. A catalyst system comprising:

(a) a source of group VIII metal cations;

(b) a bidentate ligand of claim 1; and (c) a source of anions.

12. The catalyst system of claim 11 wherein the substituents of the bidentate ligand are substituted at carbon atoms of the bridging group connected with the atoms $M^1$ and $M^2$.

13. The catalyst system of claim 11 wherein the bridging group of the bidentate ligand contains from 2 to 4 carbon atoms in the bridge.

14. The catalyst system of claim 11 wherein both $M^1$ and $M^2$ of the bidentate ligand are phosphorus atoms.

15. The catalyst system of claim 12 wherein the substituents of the bidentate ligand are alkyl groups.

16. The catalyst system of claim 11 wherein $R^1$ and $R^2$ and/or $R^3$ and $R^4$ of the bidenate ligand together represent a bivalent substituted or non-substituted cycloalkylene group having from 6 to and including 9 ring atoms, whereby the two free valencies are linked to $M^1$ or $M^2$.

17. The catalyst system of claim 11 wherein the metals of the source of group VIII metal cations is selected from the group consisting of rhodium, nickel, palladium, platinum, and mixtures thereof.

18. The catalyst system of claim 17 wherein the metals of the source of group VIII metal cations is palladium and/or platinum.

19. A process for the carbonylation of optionally substituted ethylenically or acetylenically unsaturated compounds comprising reacting the unsaturated compounds with carbon monoxide and a coreactant in the presence of a catalyst system of claim 11 under conditions effective to carbonylate the unsaturated bonds of the unsaturated compounds.

20. The process of claim 19 wherein hydrogen is used as coreactant.

21. The process of claim 19 wherein a nucleophilic compound having a mobile hydrogen atom is used as coreactant.

22. The process of claim 19 wherein the reaction is carried out at a temperature within the range of from about 50 to about 200° C.

23. A process for the carbonylation of optionally substituted ethylenically or acetylenically unsaturated compounds comprising reacting the unsaturated compounds with carbon monoxide and a coreactant in the presence of a catalyst system of claim 12 under conditions effective to carbonylate the unsaturated bonds of the unsaturated compounds.

24. The process of claim 23 wherein hydrogen is used as coreactant.

25. The process of claim 23 wherein a nucleophilic compound having a mobile hydrogen atom is used as coreactant.

26. A process for the carbonylation of optionally substituted ethylenically or acetylenically unsaturated compounds comprising reacting the unsaturated compounds with carbon monoxide and a coreactant in the presence of a catalyst system of claim 14 under conditions effective to carbonylate the unsaturated bonds of the unsaturated compounds.

27. The process of claim 26 wherein hydrogen is used as coreactant.

28. The process of claim 26 wherein a nucleophilic compound having a mobile hydrogen atom is used as coreactant.

29. The process of claim 26 wherein the reaction is carried out at a temperature within the range of from about 50 to about 200° C.

30. A process for the hydroformylation of optionally substituted ethylenically or acetylenically unsaturated compounds comprising reacting the unsaturated compounds with carbon monoxide and hydrogen in the presence of a catalyst system of claim 11 under conditions effective to carbonylate the unsaturated bonds of the unsaturated compounds.

31. A process for the hydroformylation of optionally substituted ethylenically or acetylenically unsaturated compounds comprising reacting the unsaturated compounds with carbon monoxide and hydrogen in the presence of a catalyst system of claim 12 under conditions effective to carbonylate the unsaturated bonds of the unsaturated compounds.

32. A process for the hydroformylation of optionally substituted ethylenically or acetylenically unsaturated compounds comprising reacting the unsaturated compounds with carbon monoxide and hydrogen in the presence of a catalyst system of claim 14 under conditions effective to carbonylate the unsaturated bonds of the unsaturated compounds.

* * * * *